(12) United States Patent
Campbell et al.

(10) Patent No.: US 10,299,950 B2
(45) Date of Patent: May 28, 2019

(54) STENT DELIVERY SYSTEM

(71) Applicant: Cook Medical Technologies LLC, Bloomington, IN (US)

(72) Inventors: Triona Campbell, Co Tipperary (IE); Colm McElligott, Limerick (IE); Melissa Anenden, Queensland (AU); Gerard Treacy, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 153 days.

(21) Appl. No.: 15/158,844

(22) Filed: May 19, 2016

(65) Prior Publication Data

US 2016/0338865 A1 Nov. 24, 2016

Related U.S. Application Data

(60) Provisional application No. 62/164,260, filed on May 20, 2015.

(51) Int. Cl.
*A61F 2/966* (2013.01)
*A61F 2/95* (2013.01)
*A61F 2/82* (2013.01)

(52) U.S. Cl.
CPC ............ *A61F 2/966* (2013.01); *A61F 2/82* (2013.01); *A61F 2002/9511* (2013.01); *A61F 2002/9665* (2013.01); *A61F 2230/0069* (2013.01)

(58) Field of Classification Search
CPC ............. A61F 2/966; A61F 2002/9511; A61F 2002/9665
See application file for complete search history.

(56) References Cited

U.S. PATENT DOCUMENTS 6,168,616 B1    1/2001  Brown, III
6,468,298 B1 *  10/2002  Pelton ................ A61F 2/95
                                                       606/194

(Continued)

FOREIGN PATENT DOCUMENTS

JP          2006346350 A    12/2006
WO    WO 2008/098255 A2     2/2008

(Continued)

OTHER PUBLICATIONS

International Search Report for related application No. PCT/US2016/033228, dated Jul. 27, 2016 (4 pgs).

(Continued)

*Primary Examiner* — Alexander J Orkin
(74) *Attorney, Agent, or Firm* — Brinks Gilson & Lione (57) ABSTRACT

A stent delivery system is provided that includes an inner elongate shaft with a lumen and an outer elongate shaft with a lumen, where the inner elongate shaft coaxially extends at least partially within the lumen of the outer elongate shaft. The stent delivery system also a pull member movably disposed along the the inner elongate shaft and first and second restraining members removably secured to the pull member. The stent delivery system also includes a self-expanding stent having an expanded configuration and a collapsed configuration, where the first restraining member is secured to a first portion of the self-expanding stent and the second restraining member is secured to a second portion of the self-expanding stent, thereby securing the self-expanding stent about the outer elongate shaft. Movement of the inner and elongate shafts relative to each other in a first direction applies a tension to the first and second restraining members to move the self-expanding stent to the collapsed configuration.

19 Claims, 6 Drawing Sheets

(56) References Cited

U.S. PATENT DOCUMENTS

| | | | |
|---|---|---|---|
| 6,764,503 B1* | 7/2004 | Ishimaru | A61F 2/07 606/108 |
| 2003/0225445 A1* | 12/2003 | Derus | A61F 2/95 623/1.11 |
| 2005/0090834 A1* | 4/2005 | Chiang | A61F 2/07 606/108 |
| 2005/0119722 A1* | 6/2005 | Styrc | A61F 2/95 623/1.12 |
| 2008/0071343 A1* | 3/2008 | Mayberry | A61F 2/954 623/1.11 |
| 2008/0140178 A1 | 6/2008 | Rasmussen et al. | |
| 2009/0048656 A1* | 2/2009 | Wen | A61F 2/2418 623/1.12 |
| 2009/0099640 A1 | 4/2009 | Weng | |
| 2010/0082089 A1* | 4/2010 | Quadri | A61F 2/2418 623/1.11 |
| 2010/0262157 A1* | 10/2010 | Silver | A61F 2/95 606/108 |
| 2010/0268317 A1* | 10/2010 | Stiger | A61F 2/95 623/1.12 |
| 2011/0190865 A1* | 8/2011 | McHugo | A61F 2/95 623/1.11 |
| 2013/0006347 A1 | 1/2013 | McHugo | |

FOREIGN PATENT DOCUMENTS

| | | |
|---|---|---|
| WO | WO 2010/040009 A1 | 10/2009 |
| WO | WO 2011/094527 A1 | 1/2011 |
| WO | WO 2012/082453 A1 | 12/2011 |
| WO | WO 2013/003170 A1 | 6/2012 |

OTHER PUBLICATIONS

PCT Written Opinion of ISA for related application No. PCT/US2016/033228, dated Jul. 27, 2016 (11 pgs).

* cited by examiner

STENT DELIVERY SYSTEM

CROSS-REFERENCE TO RELATED APPLICATIONS

The present patent document claims the benefit of the filing date under 35 U.S.C. § 119(e) of Provisional U.S. Patent Application Ser. No. 62/164,260 filed May 20, 2015, which is hereby incorporated by reference.

TECHNICAL FIELD

This disclosure relates to a medical device and, in particular to a device for delivering and deploying a self-expanding stent and a method of delivering and deploying the stent into a body lumen.

BACKGROUND

Self-expanding stents are medical devices used to treat diseased areas of a variety of body lumens, including, but not limited to: veins, esophagi, bile ducts, colons, and ureters. Generally, self-expanding stents are used to support a weak point in the body lumen or to bypass it completely. A self-expanding stent is a tubular structure with at least one lumen that runs through it. Self-expanding stents are often made of a wire or mesh material that can elastically contract and expand.

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling the outer sheath relative to the inner catheter until the stent is exposed. The self-expanding stent then expands from the stent distal end to the stent proximal end as the sheath is proximally withdrawn.

Several problems may occur with the sheathed delivery device described above. Sheath release delivery devices are difficult to reposition or remove and slow to operate. Often, the stent is first partially deployed to determine whether the stent is properly positioned within the body lumen. Partial deployment is achieved by withdrawing the outer sheath so that only a portion of the self-expanding stent is exposed. The stent may then be reconstrained by pushing the outer sheath back over the entire length of the stent, thus allowing the stent to be repositioned or removed. However, once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded in the body lumen. Additionally, retraction of the outer sheath with controlled movement may not be achieved because the physician is manually retracting the outer sheath which may lead to uneven or inadvertent movement of the outer sheath that can lead to improper positioning of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications such as to prevent stent migration. Additionally, conventional sheathed stent delivery systems may cause problems where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically strong enough to overcome the frictional forces between the sheath and the stent to avoid undesirable frictional consequences such as stretching of the introducer catchers and hysterics in the movement of the stent. The sheathed stent delivery device also requires more space within an endoscope compared to a sheathless device and also adds additional expense to the delivery system.

Accordingly, in view of the drawbacks of current technology, there is a desire for a delivery system that can increase the control, accuracy and ease of placement of a stent during deployment of the stent within a lumen within a patient. The delivery system would ideally reduce the risk of malfunction while providing for a smoother, more accurate and quicker deployment of the entire stent. The delivery system also would provide the ability to recollapse, recapture, reposition and/or remove the stent after expansion of the stent.

BRIEF SUMMARY

In one aspect, a stent delivery system is provided. The system comprises an inner elongate shaft comprising a lumen extending at least partially therethrough and an outer elongate shaft comprising a lumen extending at least partially therethrough. The inner elongate shaft coaxially extends at least partially within the lumen of the outer elongate shaft and the inner and outer elongate shafts are movably positionable relative to each other. The system also comprises a pull member movably disposed along the inner elongate shaft. The system further comprises a first restraining member removably secured to the pull member and a second restraining member removably secured to the pull member. Additionally, the system comprises a self-expanding stent having an expanded configuration and a collapsed configuration, wherein the first restraining member is secured to a first portion of the self-expanding stent and the second restraining member is secured to a second portion of the self-expanding stent, thereby securing the self-expanding stent about the outer elongate shaft. In the stent delivery system, movement of the inner and outer elongate shafts relative to each other in a first direction applies a tension to the first and second restraining members to move the self-expanding stent to the collapsed configuration.

The outer elongate shaft of the stent delivery system may further comprises a notch on a longitudinal side of the outer elongate shaft, the notch allowing communication between the lumen of the outer elongate shaft and a point external to the outer elongate shaft, wherein the second restraining member extends through the notch. The system may also comprise wherein the second restraining member is removably secured to the pull member at a point proximal to a proximal end of the inner elongate shaft. Also, the first restraining member of the stent delivery system may be removably secured to the pull member at a point distal to a distal end of the inner elongate shaft and a distal end of the outer elongate shaft. The system may also comprise an end cap attached to a distal portion of the inner elongate shaft, wherein a distal portion of the pull member is removably secured to the end cap. Additionally, the system may comprise a cannula attached to an extending from a proximal end of the inner elongate shaft. The stent delivery system may further comprise a handle comprising a first arm attached to a proximal portion of the cannula and a second arm attached to a proximal portion of the outer catheter, wherein movement of the first arm with respect to the second arm causes corresponding movement of the cannula with respect to the outer catheter. The system may also comprise a locking member attached to the handle having a locked configuration and a released configuration, wherein movement of the inner elongate shaft relative to the outer elongate shaft is restricted when the locking member is in the locked configuration.

In another aspect of the invention, a method of delivering a stent is provided. The method comprises inserting a distal portion of a stent delivery system into a body lumen of a patient, the stent delivery system comprising an inner elongate shaft comprising a lumen extending at least partially therethrough and an outer elongate shaft comprising a lumen extending at least partially therethrough, wherein the inner elongate shaft coaxially extends at least partially within the lumen of the outer elongate shaft, and the inner and outer elongate shafts are movably positionable relative to each other. The system also comprises a pull member movably disposed within the lumen of the inner elongate shaft. The stent delivery system further comprises a first restraining member removably secured to the pull member and a second restraining member removably secured to the pull member. Additionally, the system comprises a self-expanding stent having an expanded configuration and a collapsed configuration, wherein the first restraining member is secured to a first portion of the self-expanding stent and the second restraining member is secured to a second portion of the self-expanding stent, thereby securing the self-expanding stent about the outer elongate shaft. The method further comprises maintaining the self-expanding stent in a collapsed configuration with the inner and outer elongate shafts in a first position and tension applied to the first and second restraining members for delivery of the self-expanding stent to an implant site. The method also comprises positioning the self-expanding stent at the implant site and expanding the self-expanding stent to the expanded configuration by moving the inner and outer elongate shafts relative to each other to a second position and releasing tension on the first and second restraining members so that the self-expanding stent moves to the expanded configuration.

DETAILED DESCRIPTION

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

As used in the specification, the terms proximal and distal should be understood as being in the terms of a physician using the delivery system. Hence the term distal means the portion of the delivery system which is farthest from the physician and the term proximal means the portion of the delivery system which is nearest to the physician.

Figure 1:
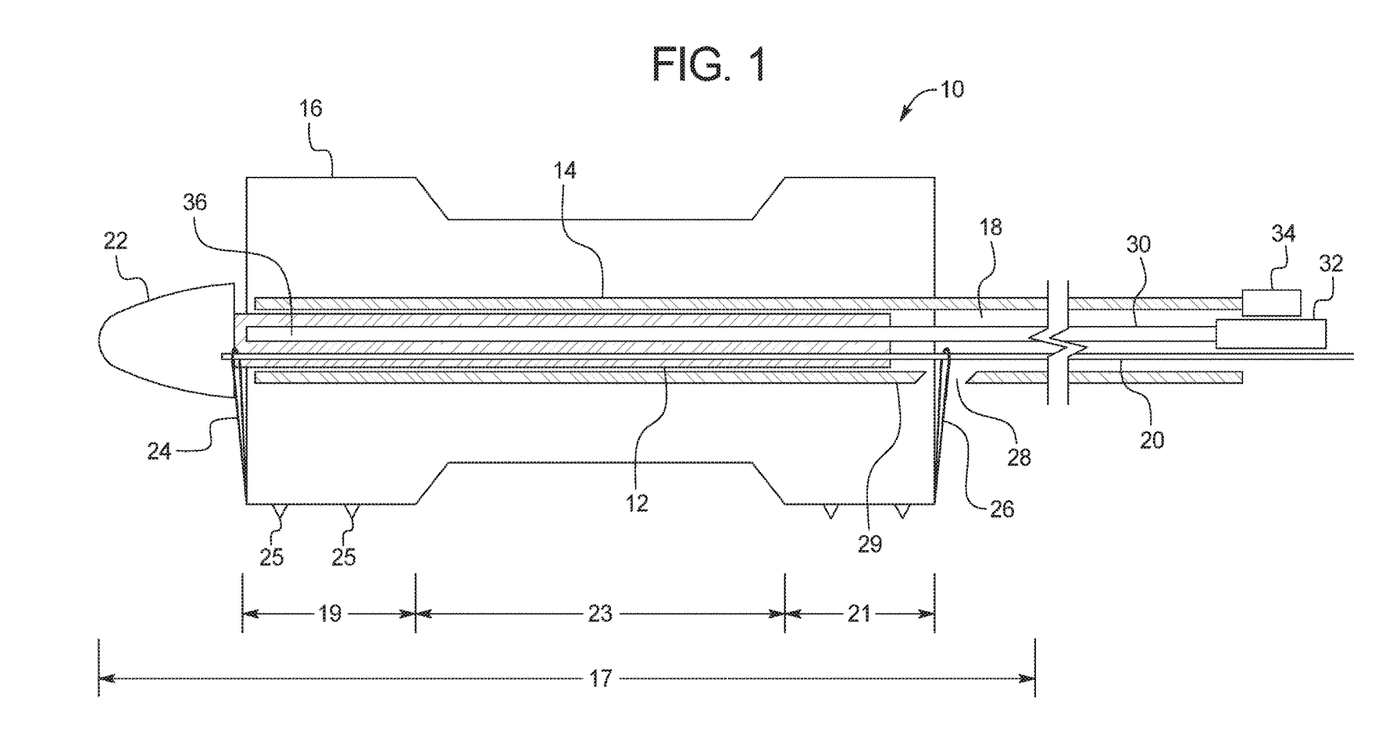
FIG. 1 is a cross-sectional side view of a stent delivery system according to an embodiment of the present invention illustrating a stent in an expanded configuration.
Figure 2:
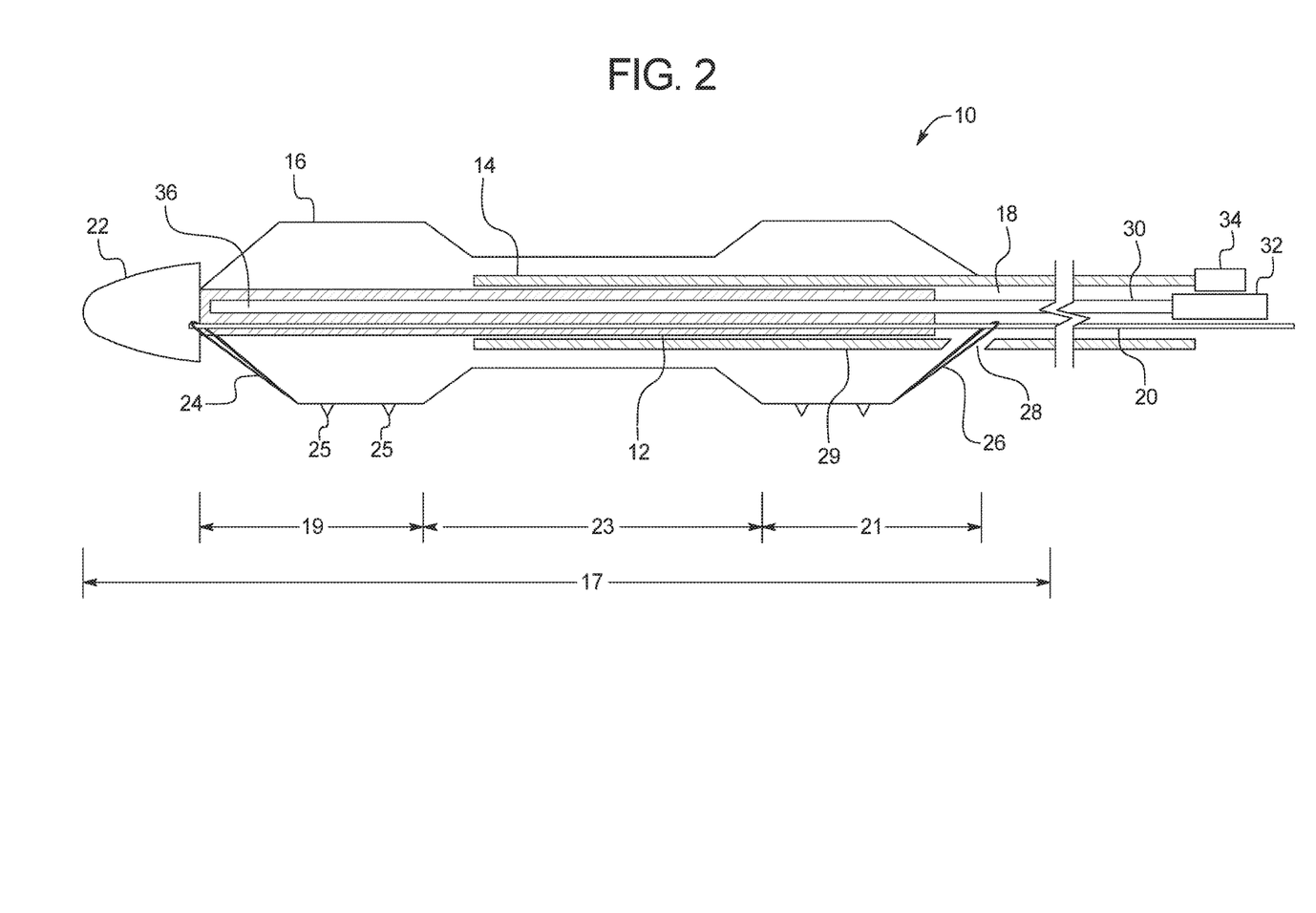
FIG. 2 is a cross-sectional side view of the stent delivery system shown in FIG. 1 illustrating the stent in a collapsed configuration.

FIGS. 1 and 2 illustrate a cross sectional view of a stent delivery system 10 in accordance with embodiments of the present invention. FIG. 1 shows the stent delivery system 10 in an expanded configuration while FIG. 2 shows the stent delivery system 10 in a collapsed configuration. The stent delivery system 10 includes an inner shuttle 12 and an outer catheter 14. A stent 16 is positionable about the outer catheter 14 at a distal portion 17 of the stent delivery system 10. The stent 16 is ideally a self-expanding stent and may have three sections: a distal flange 19, a proximal flange 21, and a central portion 23. The flanges 19 and 21 are designed with a larger expanded diameter that makes contact with the wall of the body lumen to secure the stent 16. The central portion 23 has a smaller outer diameter in the expanded configuration that does not make contact with the wall of the body lumen while still providing a passageway to bypass the diseased area. The stent 16 may be stepped, tapered, or have any other contemplated transition from the central portion 23 to the flanges 19 and 21. While the flanges 19 and 21 help prevent the migration of the stent 16 after the stent 16 has been fully deployed, the flanges 19 and 21 may also have barbs 25 or some other structure that helps secure the stent 16 to the body lumen wall, including, but not limited to, adhesives. The outer catheter 14 is an elongate tube with a lumen 18 within which the inner shuttle 12, another elongate tube, is coaxially positioned. The inner shuttle 12 is longitudinally movable within the lumen of the outer catheter 14. The inner shuttle 12 may have a lumen within which a pull member 20 is movably disposed. The pull member 20 ideally extends from at least the distal end of the inner shuttle 12 to a point external from the patient when the stent 16 is positioned at the diseased area. An end cap 22 may be attached to the distal end of the inner shuttle 12. The end cap 22 typically has an atraumatic conical or rounded shape;

however other shapes may be used. A distal portion of the pull member 20 may be temporarily secured to the end cap 22 so that longitudinal movement of the pull member 20 with respect to the inner shuttle 12 is restricted. The pull member 20 may also be designed to be detachable from the end cap 22 by way of a deliberate action by the physician.

The stent delivery system 10 ideally includes two restraining members, although additional restraining members may be used. In this embodiment, the restraining members are suture loops, however a variety of designs are contemplated. The first restraining member 24 may be located near the distal end of the stent delivery system. The pull member 20 is threaded through the restraining member 24 and another portion of the first restraining member 24 is attached to the stent 16. The point at which the pull member 20 is threaded through the first restraining member 24 is ideally at a point distal the distal ends of the outer catheter 14 and inner shuttle 12, but proximal the end cap 22; however, other designs are contemplated. The second restraining member 26 may be located proximal to the first restraining member 24. The pull member 20 is threaded through the second restraining member 26 and another portion of the second restraining member 26 is attached to the stent 16. Since the outer catheter 14 ideally extends proximally to a point external from the patient when the stent 16 is located at the diseased site, a notch 28 may be in a portion of the wall 29 of the outer catheter 14. The notch 28 allows access into the lumen 18 of the outer catheter 14 so that the second restraining member 26 may be secured to both the pull member 20 and the stent 16. The point at which the pull member 20 is threaded through the second restraining member 26 is ideally at a point proximal the proximal end of the inner shuttle 12.

As described above, the inner shuttle 12 is longitudinally movable within the lumen 18 of the outer catheter 14. When the inner shuttle 12 and the outer catheter 14 are in a first position as shown in FIG. 1, the stent 16 is in an expanded configuration. When the inner shuttle 12 is moved distally with respect to the outer catheter 14, the pull member 20, and by extension the restraining members 24 and 26, tend to move distally as well. However, while the first restraining member 24 move freely with the inner shuttle 12, the movement of the second restraining member 26 is restricted by the wall 29 of the outer catheter 14. Thus, the second restraining member 26 remains in substantially the same position with respect to the outer catheter 14 while the inner shuttle 12 pushes the first restraining member 24 distally with respect to the outer catheter 14. During this movement, the restraining members 24 and 26 apply tension in opposite directions to the stent 16, with the first restraining member 24 applying tension in a distal direction and the second restraining member 26 applying tension in a proximal direction. This tension causes the stent 16 to elongate and therefore axially collapse. Once the inner shuttle 12 and outer catheter 14 are in a second position, the stent 16 is fully stretched into the collapsed configuration as shown in FIG. 2.

The stent 16 has a lower axial profile in the collapsed configuration, and therefore it can be inserted into the patient's body lumen with greater ease than when the stent 16 is in the expanded configuration. The stent delivery system 10 is repeatedly movable between the expanded and collapsed configurations by moving the outer catheter 14 and inner shuttle 12 longitudinally with respect to each other. The stent 16 may be permanently expanded or deployed by retracting the pull member 20 from the stent delivery system 10. As the pull member 20 is retracted, the restraining members 24 and 26 are detached from the pull member 20, thus freeing the stent 16 from the stent delivery system 10 and allowing the stent 16 to fully and permanently expand. The stent 16 is ideally a self-expandable woven or braided stent, thus allowing the stent 16 to automatically expand once freed from about the stent delivery system 10. By way of non-limiting example, the stent 16 may be formed as a woven or braided mesh formed from a metal or polymer or a laser cut pattern formed in a metal stent. The stent delivery system 10 uses the axial elongation of compressed woven, braided, or laser cut stents, normally considered a disadvantage, as an advantage to eliminate the need for a delivery sheath. The stent may also be formed from a bioabsorbable material. One example of a woven stent is the EVOLUTION® stent (Wilson-Cook Medical, Inc.).

The restraining members 24 and 26 may each be attached to the stent 16 at single points, or they may be woven through the respective crowns 19 and 21 of the stent 16. For example, the first restraining member 24 may be woven through the entire circumference of the distal crown 19, thus creating a more secure connection between the first restraining member 24 and stent 16. Additionally, when tension is applied to the restraining members 24 and 26, the ends of the stent 16 will radially close in addition the stent 16 elongating and collapsing, which may be advantageous to prevent the barbs 25 from prematurely contacting the wall of the body lumen. Also, in the embodiment of FIGS. 1 and 2, the restraining members 24 and 26 are suture loops. The suture loops may have a diameter that is large enough to not constrain the crowns 19 and 21 when the stent delivery system 10 is in the expanded configuration. However, it may also be advantageous for the suture loops to have a smaller diameter that still partially constrains the crowns 19 and 21 of the stent 16 when the stent delivery system is in the expanded configuration, thus preventing the crowns 19 and 21 from contacting the wall of the body lumen. However, due to the contraction of the stent 16 when moved to the expanded configuration, the central portion 23 will still fully expand as it is not radially constrained by any restraining members. Thus, the central portion 23 may be expanded first, and then, once the physician is ready to permanently expand the stent 16, the pull member 20 may be removed allowing the crowns 19 and 21 to fully expand as well.

The stent delivery system 10 may also include a cannula 30 secured to the inner shuttle 14 such that longitudinal movement of the inner shuttle 14 can be controlled with longitudinal movement of the cannula 30. The cannula 30 may extend from a proximal portion of the inner shuttle 14 to a point external from the patient. Thus, the cannula 30 may be used to manipulate the stent delivery system 10 between an expanded configuration and a collapsed configuration. To further ease manipulation between the two configurations, a handle 32 may be attached to the cannula 30. A handle 34 may also be attached to the outer catheter 14. The stent delivery system 10 may include a lock 37 to releasably lock the handles 32 and 34 in the first position or the second position. In some embodiments, the lock 37 may be positionable so that the relative position of the inner shuttle 12 and outer catheter 14 may be releasably locked in any longitudinal position. The inner shuttle 14 and cannula 30 may additionally include a wire guide lumen 36. A wire guide may then be inserted into the patient's body lumen prior to the stent delivery system 10 to assist in guiding the stent delivery system 10 to the diseased site. The stent delivery system 10 may also include radiopaque markers on the stent 16 or other parts of the stent delivery system 10 to assist the physician in placement of the stent 16.

Figure 3:
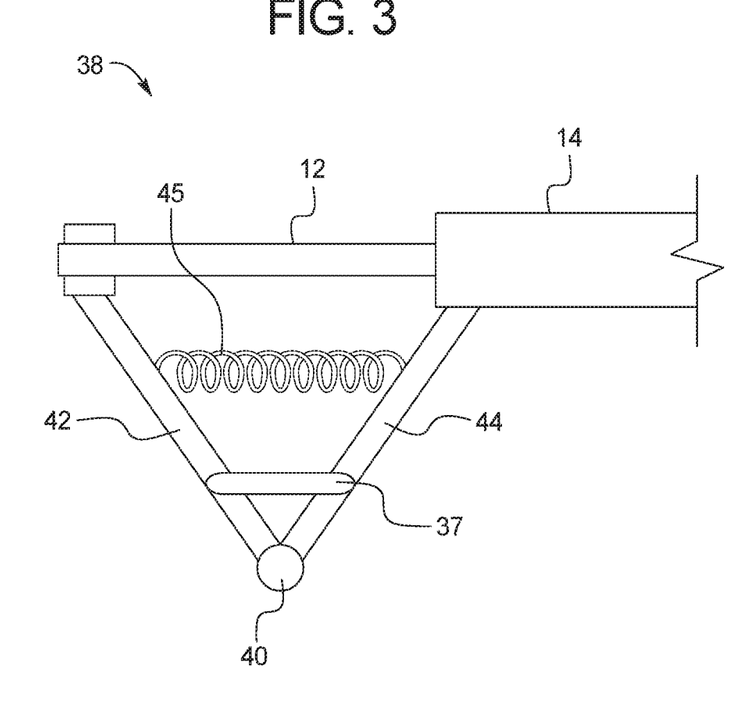
FIG. 3 is a side view of an embodiment of a handle of the stent delivery system according to an embodiment of the present invention.

The relative movement of the stent delivery system 10 illustrated in FIGS. 1 and 2 is shown by way of example and meant to be non-limiting. Other configurations for the arrangement of the connection of the stent to the inner shuttle and outer catheter for moving the stent between the collapsed and expanded configurations are also possible. For example, a single handle 38 may be used in lieu of the individual handles 32 and 34 described previously. As shown in FIG. 3, a hinge 40 allows the left arm 42 and right arm 44 of the single handle 38 to pivot with respect to each other, thus allowing the outer catheter 14 and inner shuttle 12 to move correspondingly. Thus, the physician may use the handle 38 to easily move the stent delivery system 10 between a collapsed configuration and an expanded configuration. A lock 37 may be used as described previously. The single handle 38 may also include a spring 45 or other biasing member to bias the single handle 38 in a certain position. In one embodiment, the spring 45 may bias the stent delivery system 10 towards a collapsed configuration, thus requiring deliberate manipulation of the handle by the physician to move the stent delivery system 10 into an expanded configuration. Alternatively, the spring 45 may bias the stent delivery system 10 towards an expanded configuration.

Figure 4:
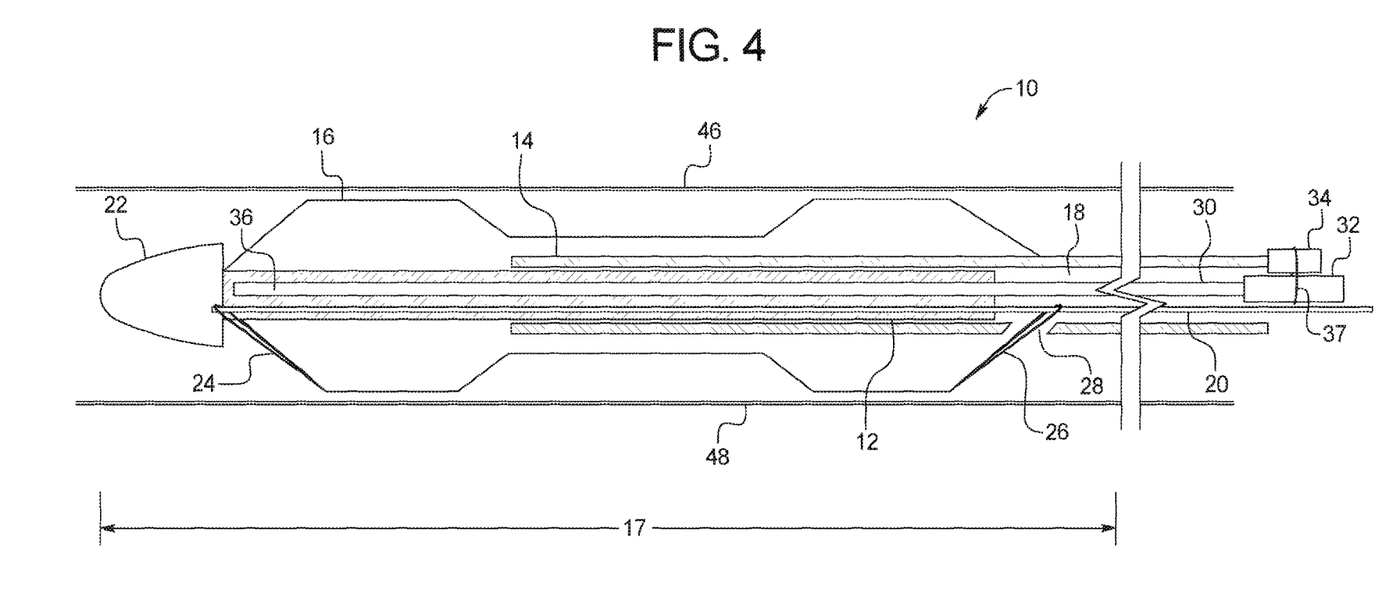
FIG. 4 is a cross-sectional side view of a stent delivery system with a delivery sheath.

The stent delivery system 10 may optionally include a delivery sheath 46 slidably positionable over a portion of the outer catheter 14 and the inner shuttle 12 to cover the stent 16 as shown in FIG. 4. The optional delivery sheath 46 is shown extended distally over the stent 16 forming a smooth outer surface 48 of the delivery system 10. The delivery sheath 46 may be provided to facilitate a smoother delivery of the stent 16 to the desired location and is not required for collapsing the stent 16 in the collapsed configuration. For example, the smooth outer surface 48 may prevent damage to the walls of the body lumen or damage to the stent 16 while the stent delivery system 10 is being inserted into the body lumen. When present, the delivery sheath 46 may provide some compressive force to the stent 16. The delivery sheath 46 may be operably connected to a handle to provide longitudinal movement of the delivery sheath 46 to expose the stent 16. Once the stent delivery system 10 is at the desired location, the delivery sheath 46 may be removed by sliding the delivery sheath 46 proximally with respect to the outer catheter 14 until the delivery sheath 46 has been withdrawn from the patient's body lumen. Once the delivery sheath 46 is removed, the stent delivery system 10 may be used as previously described.

Figure 5:
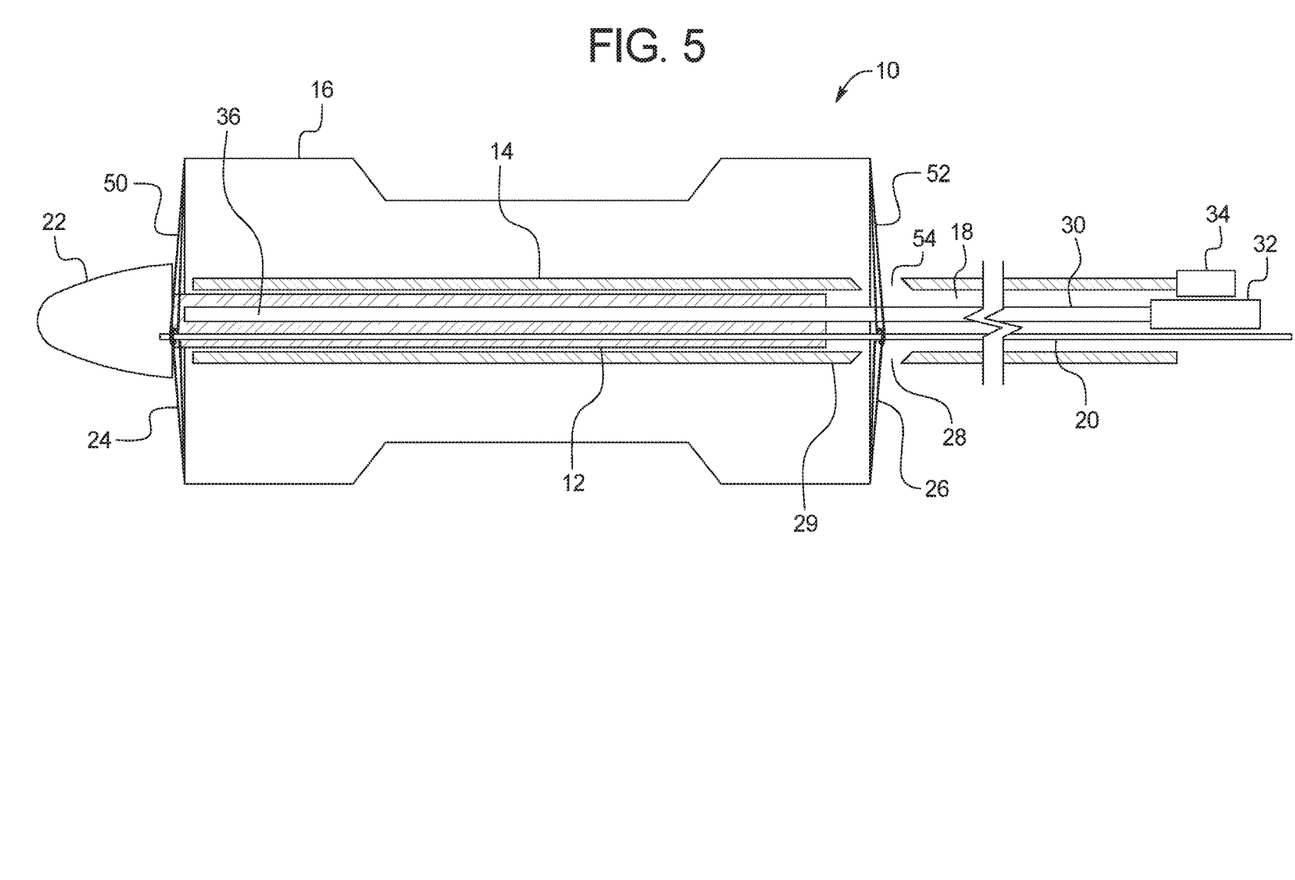
FIG. 5 is a cross-sectional side view of a stent delivery system with additional restraining members.

While the previously described embodiments describe the use of only two restraining members, more restraining members may be used. For example, FIG. 5 shows two additional restraining members: a third restraining member 50 and a fourth restraining member 52. The pull member 20 may be threaded through the third restraining member 50 near where the pull member 20 is threaded through the first restraining member 24, and the pull member 20 may be threaded the fourth restraining member 52 near where the pull member 20 is threaded through the second restraining member 26. Similar to the notch 28 in the wall 29 of the outer catheter 14 that allows the second restraining member 26 to be attached to the stent 16 and the pull member 20, a second notch 54 may be used for the fourth restraining member 52. Alternatively, the fourth restraining member 52 may be threaded through the original notch 28 and around the outside wall 29 of the outer catheter 14 to a point where it connects to the stent 16. However, this design may cause undesirable torsional forces on the stent 16. When additional restraining members are used, the tension applied to the stent 16 by the restraining members is more uniform. For example, tension is applied to two points on the stent 16 when only two restraining members are used as shown in FIGS. 1 and 2, which may cause a large amount of stress on those two points, potentially leading to plastic deformation of the stent. However, in the FIG. 5 embodiment, tension is applied to four points on the stent 16, thus reducing the stress on each individual attachment point. The additional points of contact may allow the stent 16 to have a lower, more uniform axial profile when in the collapsed configuration. While FIG. 5 shows the stent delivery system 10 with a total of four restraining members, additional restraining members may be used. For example, restraining members may be attached to the stent 16 at an intermediate location, thus further securing the stent 16 about the outer sheath 14. If restraining members are used at an intermediate location, then additional notches in the outer sheath 14 may be used to allow communication between the restraining members and the pull member 20.

Figure 6:
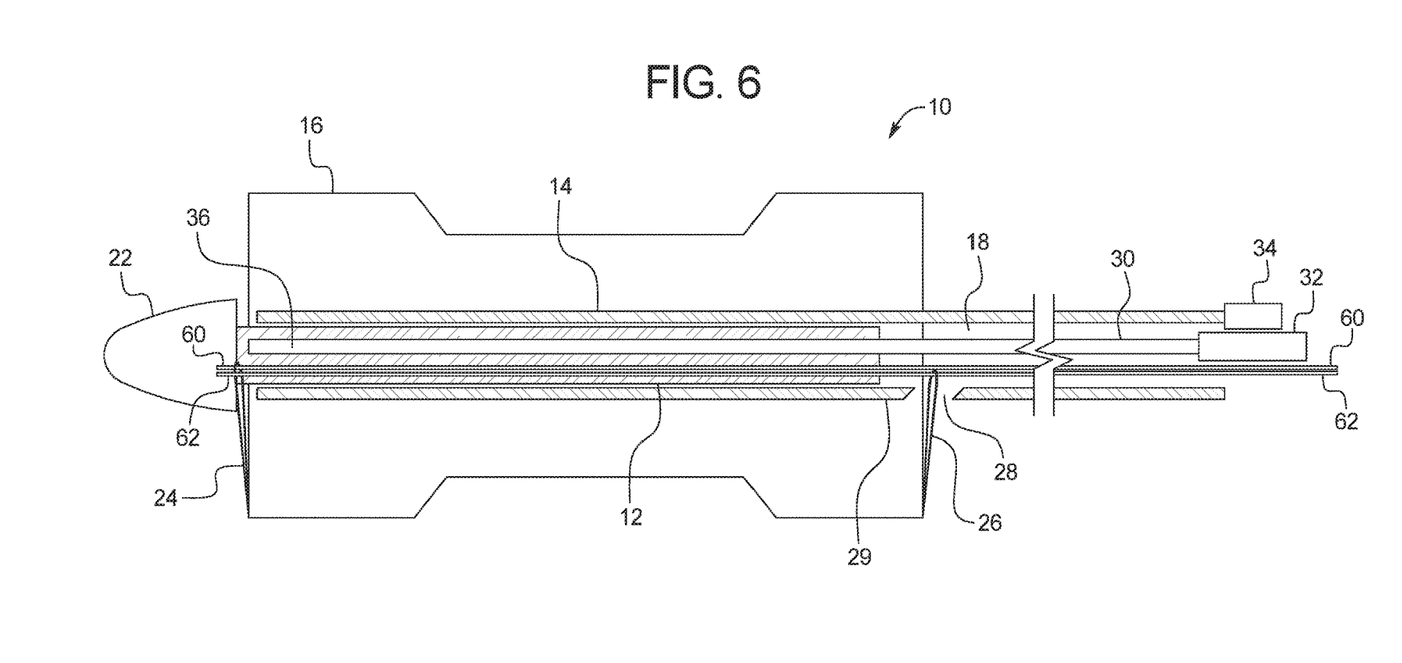
FIG. 6 is a cross-sectional side view of a stent delivery system with multiple pull members.

Additionally, multiple pull members may be used as shown in FIG. 6. For example, a first pull member 60 and a second pull member 62 may be used. The first pull member 60 may be threaded through the first restraining member 24 while the second pull member 62 may be threaded through the second restraining member 26. The pull members 60 and 62 may be disposed within the same lumen of the inner shuttle 12 or separate lumens. Both pull members may be removably secured to the end cap 22 of the inner shuttle 12. The pull members 60 and 62 can then be individually removed to allow the physician to control which portion of the stent 16 is expanded first. For example, the physician may remove the second pull member 62 first, thus allowing the proximal portion of the stent 16 to expand before removing the first pull member 60 to allow the rest of the stent 16 to fully expand. In accordance with the ideas of this invention, any number of pull members used with any number of restraining members is contemplated.

In some embodiments, the restraining members 24 and 26 may remain attached to the stent 16 after the stent delivery system 10 is withdrawn. The restraining members 24 and 26 may be designed to be biodegradable. Additionally, while this embodiment utilizes restraining members 24 and 26 that are suture loops to secure the stent 16 to the pull member 20, any type of mechanism that can releasably hold the stent 16 in an expanded and collapsed configuration may be used. By way of non-limiting example, the restraining members 24 and 26 may be substituted with releasable bands, hooks, adhesives, wires, and the like.

The materials used to manufacture the components of the stent delivery systems described herein may be any materials known to one skilled in the art that are suitable for use in patients. By way of non-limiting example, the inner shuttle, outer catheter and delivery sheath may be formed from polytetrafluoroethylene (PTFE) particularly when a low friction delivery sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments.

The stent may be formed from but is not limited to the following materials: Nickel titanium alloys, for example, nitinol, stainless steel, cobalt alloys and titanium alloys. The wires may be made from a metallic alloy such as stainless steel or nickel titanium. In some embodiments, the pull member and restraining members may be made from polymers having sufficient strength to hold the stent in the collapsed configuration. The pull member and restraining members may be single, multiple, braided or twisted. In some embodiments, the pull member and restraining members or segments thereof may be coated, for example with a coating such as PTFE. In some embodiments, the stent and/or the restraining members may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyanates; polyphosphazines; polyethers including polyglycols, polyorthoesters; epoxy polymers including polyethylene oxide; polysaccharides including cellulose, chitin, dextran, starch, hydroxyethyl starch, polygluconate, hyaluronic acid; polyamides including polyamino acids, polyesteramides, polyglutamic acid, poly-lysine, gelatin, fibrin, fibrinogen, casein, collagen.

Other suitable biocompatible materials may also be used for any of the components described herein.

Operation of the stent delivery system 10 of the present invention is described with reference to the stent delivery system 10 by way of non-limiting example. Alternative methods of operating the system may also be used. The stent delivery system 10 may be provided in a sterile packaging. The stent 16 may be provided in the expanded configuration or collapsed configuration within the packaging. For example, some stent materials may weaken or otherwise deform when stored in a collapsed configuration during shipping and storage. The stent 16 may be provided in the expanded configuration and be moved to the collapsed configuration to the first position shown in FIG. 1 prior to delivery into the patient.

The delivery system 10 may be delivered to the patient using an endoscope that may be positioned within the body lumen so the operator can view a proximal side of the diseased area to be treated with the stent 16. The operator inserts the distal portion 17 of the stent delivery system 10 into the patient's body lumen with the stent 16 in the collapsed configuration. A wire guide may be inserted first to assist in navigating the endoscope to the diseased site and the system 10 is then delivered through the working channel of the endoscope over the wire guide to the diseased site. Alternatively, the stent delivery system 10 may be inserted into the patient's lumen without the use of an endoscope, depending on the size and location of the lumen.

The collapsed stent 16 may be moved within the body lumen to correctly position the stent 16 at the diseased site. The stent 16 is moved to the expanded configuration by movement of the inner shuttle 12 relative to the outer catheter 14 to release the tension on the restraining members 24 and 26, for example by moving the outer catheter 14 distally and/or the inner shuttle 12 proximally. The position of the expanded stent 16 can be monitored through fluoroscopy or other methods well known in the art. If necessary, such as if the stent 16 is incorrectly positioned, the physician may return the stent 16 to the collapsed configuration by moving the inner shuttle 12 distally and or the outer catheter 14 proximally to return the tension to the restraining members 24 and 26 and collapse the stent 16 about the outer catheter 14. The stent 16 may be moved from the collapsed configuration to the expanded configuration as many times as needed.

Once proper position for the stent 16 is achieved within the patient's body lumen, the pull member 20 may be withdrawn to release the restraining members 24 and 26 and therefore the stent 16 from about the outer catheter 14, thus allowing the stent 16 to fully expand in the body lumen. The delivery system 10 may then be withdrawn proximally from the patient.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system, comprising:
an inner elongate shaft comprising a lumen extending at least partially therethrough;
an outer elongate shaft comprising a lumen extending at least partially therethrough, the inner elongate shaft coaxially extending at least partially within the lumen of the outer elongate shaft, the inner and outer elongate shafts movably positionable relative to each other;
an elongate pull member movably disposed through the lumen of the inner elongate shaft;
a first restraining member removably secured to the pull member, the first restraining member being engaged by a distal portion of the inner elongate shaft to prevent axial movement of the first restraining member relative to the inner elongate shaft;
a second restraining member removably secured to the pull member at a location proximal to a proximal end of the lumen of the inner elongate shaft, the second restraining member extending through an opening in the outer elongate shaft, the second restraining member being engaged by the opening of the outer elongate shaft to prevent axial movement of the second restraining member relative to the outer elongate shaft; and
a self-expanding stent having an expanded configuration and a collapsed configuration, wherein the first restraining member is fixedly secured to a first portion of the self-expanding stent and the second restraining member is fixedly secured to a second portion of the self-expanding stent, thereby securing the self-expanding stent about the outer elongate shaft;
wherein movement of the inner and outer elongate shafts relative to each other in a first direction causes the first and second restraining members to move axially apart so as to apply a tension to the first and second portions of the self-expanding stent to move the self-expanding stent to the collapsed configuration.

2. The stent delivery system of claim 1, wherein:
movement of the inner and outer elongate shafts relative to each other in a second direction causes the first and second restraining members to move axially together so as to release the tension on the first and second portions of the self-expanding stent to move the self-expanding stent to the expanded configuration.

3. The stent delivery system of claim 1, wherein:
the opening in the outer elongate shaft comprises a notch on a longitudinal side of the outer elongate shaft, the notch allowing communication between the lumen of the outer elongate shaft and a point external to the outer elongate shaft, wherein the second restraining member extends through the notch.

4. The stent delivery system of claim 3, wherein: the second restraining member is removably secured to the pull member at a point proximal to a proximal end of the inner elongate shaft.

5. The stent delivery system of claim 4, wherein: the first restraining member is removably secured to the pull member at a point distal to a distal end of the inner elongate shaft and a distal end of the outer elongate shaft.

6. The stent delivery system of claim 1, wherein: the first restraining member is removably secured to the pull member at a point adjacent to both a distal end of the inner elongate shaft and a distal end of the outer elongate shaft.

7. The stent delivery system of claim 1, wherein: the inner elongate shaft further comprises a wire guide lumen extending at least partially therethrough.

8. The stent delivery system of claim 1, further comprising:
an end cap attached to a distal portion of the inner elongate shaft, wherein a distal portion of the pull member is removably secured to the end cap.

9. The stent delivery system of claim 1, further comprising:
a cannula attached to and extending from a proximal end of the inner elongate shaft, the cannula being disposed adjacent to the pull member.

10. The stent delivery system of claim 9, further comprising:
a first handle attached to a proximal portion of the cannula; and
a second handle attached to a proximal portion of the outer elongate shaft.

11. The stent delivery system of claim 10, further comprising:
a locking member attached to the first handle and the second handle having a locked configuration and a released configuration, wherein movement of the inner elongate shaft relative to the outer elongate shaft is restricted when the locking member is in the locked configuration.

12. The stent delivery system of claim 9, further comprising:
a handle comprising a first arm attached to a proximal portion of the cannula and a second arm attached to a proximal portion of the outer catheter, wherein movement of the first arm with respect to the second arm causes corresponding movement of the cannula with respect to the outer catheter.

13. The stent delivery system of claim 12, further comprising:
a locking member attached to the handle having a locked configuration and a released configuration, wherein movement of the inner elongate shaft relative to the outer elongate shaft is restricted when the locking member is in the locked configuration.

14. The stent delivery system of claim 1, wherein: the pull member is removable from the inner and outer elongate shafts to release the restraining members from the delivery system and thus the self-expanding stent from about the outer elongate shaft.

15. The stent delivery system of claim 1, wherein: the self-expanding stent is repeatedly movable between the collapsed configuration and the expanded configuration.

16. The stent delivery system of claim 1, wherein: the pull member is movably disposed within the lumen of the inner elongate shaft.

17. A method for delivering a stent, comprising:
inserting a distal portion of a stent delivery system into a body lumen of a patient, the stent delivery system comprising:
an inner elongate shaft comprising a lumen extending at least partially therethrough;
an outer elongate shaft comprising a lumen extending at least partially therethrough, the inner elongate shaft coaxially extending at least partially within the lumen of the outer elongate shaft, the inner and outer elongate shafts movably positionable relative to each other;
an elongate pull member movably disposed within the lumen of the inner elongate shaft;
a first restraining member removably secured to the pull member at a location near a distal end portion of the inner elongate shaft, the first restraining member being engaged by the distal end portion of the inner elongate shaft to prevent axial movement of the first restraining member relative to the inner elongate shaft;
a second restraining member removably secured to the pull member at a location proximal to a proximal end of the lumen of the inner elongate shaft such that the second restraining member is not engaged by the inner elongate shaft, the second restraining member extending through an opening in the outer elongate shaft, the second restraining member being engaged by a perimeter of the opening of the outer elongate shaft to prevent axial movement of the second restraining member relative to the outer elongate shaft; and
a self-expanding stent having an expanded configuration and a collapsed configuration, wherein the first restraining member is fixedly secured to a first portion of the self-expanding stent and the second restraining member is fixedly secured to a second portion of the self-expanding stent, thereby securing the self-expanding stent about the outer elongate shaft;
maintaining the self-expanding stent in a collapsed configuration with the inner and outer elongate shafts in a first position and tension applied to the first and second restraining members for delivery of the self-expanding stent to an implant site, wherein the first and second restraining members are axially spaced apart from each other a first distance when the inner and outer elongate shafts are in the first position;
positioning the self-expanding stent at the implant site; and
expanding the self-expanding stent to the expanded configuration by moving the inner and outer elongate shafts relative to each other to a second position and releasing tension on the first and second restraining members so that the self-expanding stent moves to the expanded configuration, wherein first and second restraining members are axially spaced apart from each other a second distance when the inner and outer elongate shafts are in the second position, the second distance being smaller than the first distance.

18. The method of claim 17, further comprising:
returning the inner and outer elongate shafts to the first position to move the self-expanding stent from the expanded configuration to the collapsed configuration.

19. The method of claim 17, further comprising:
releasing the self-expanding stent from about the outer elongate shaft at the implant site by proximally withdrawing the pull member from the inner and outer elongate shafts so as to remove the first and second restraining members from about the pull member.

* * * * *